(12) United States Patent
Dahl et al.

(10) Patent No.: US 7,413,857 B2
(45) Date of Patent: Aug. 19, 2008

(54) METHODS FOR USING RIBOPRIMERS FOR STRAND DISPLACEMENT REPLICATION OF TARGET SEQUENCES

(75) Inventors: Gary A. Dahl, Madison, WI (US); Jerome J. Jendrisak, Madison, WI (US); Agnes J. Radek, Madison, WI (US)

(73) Assignee: Epicentre Technologies, Madison, WI (US)

( * ) Notice: Subject to any disclaimer, the term of this patent is extended or adjusted under 35 U.S.C. 154(b) by 448 days.

(21) Appl. No.: 10/719,168

(22) Filed: Nov. 21, 2003

(65) Prior Publication Data

US 2004/0180361 A1 Sep. 16, 2004

Related U.S. Application Data

(60) Provisional application No. 60/428,013, filed on Nov. 21, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .................. 435/6, 435/91.2, 91.21; 536/24.33
See application file for complete search history.

(56) References Cited

U.S. PATENT DOCUMENTS

| | | | |
|---|---|---|---|
| 4,876,187 A | 10/1989 | Duck et al. | |
| 5,001,050 A | 3/1991 | Blanco et al. | |
| 5,011,769 A | 4/1991 | Duck et al. | |
| 5,403,711 A | 4/1995 | Walder et al. | |
| 5,523,204 A | 6/1996 | Singer et al. | |
| 5,536,649 A | 7/1996 | Fraiser et al. | |
| 5,539,082 A | 7/1996 | Nielsen et al. | |
| 5,591,609 A | 1/1997 | Auerbach | |
| 5,614,389 A | 3/1997 | Auerbach | |
| 5,624,825 A | 4/1997 | Walker et al. | |
| 5,631,147 A | 5/1997 | Lohman et al. | |
| 5,641,625 A | 6/1997 | Ecker et al. | |
| 5,648,211 A | 7/1997 | Fraiser et al. | |
| 5,660,988 A | 8/1997 | Duck et al. | |
| 5,700,922 A | 12/1997 | Cook | |
| 5,705,333 A | 1/1998 | Shah et al. | |
| 5,714,331 A | 2/1998 | Buchardt et al. | |
| 5,719,262 A | 2/1998 | Buchardt et al. | |
| 5,731,146 A | 3/1998 | Duck et al. | |
| 5,733,752 A | 3/1998 | Lohman et al. | |
| 5,736,336 A | 4/1998 | Buchardt et al. | |
| 5,744,308 A | 4/1998 | Guillou-Bonnici et al. | |
| 5,744,311 A | 4/1998 | Fraiser et al. | |
| 5,756,702 A | 5/1998 | Lohman et al. | |
| 5,773,571 A | 6/1998 | Nielsen et al. | |
| 5,773,733 A | 6/1998 | Tuan et al. | |
| 5,786,183 A | 7/1998 | Ryder et al. | |
| 5,786,461 A | 7/1998 | Buchardt et al. | |
| 5,817,811 A | 10/1998 | Breipohl et al. | |
| 5,834,202 A | 11/1998 | Auerbach | |
| 5,837,459 A * | 11/1998 | Berg et al. ..................... 435/6 |
| 5,849,547 A | 12/1998 | Cleuziat et al. | |
| 5,874,260 A | 2/1999 | Cleuziat et al. | |
| 5,916,779 A | 6/1999 | Pearson et al. | |
| 5,925,517 A | 7/1999 | Tyagi et al. | |
| 5,977,296 A | 11/1999 | Nielsen et al. | |
| 5,985,563 A | 11/1999 | Hyldig-Nielsen et al. | |
| 5,986,053 A | 11/1999 | Ecker et al. | |
| 6,001,567 A | 12/1999 | Brow et al. | |
| 6,015,887 A | 1/2000 | Teng | |
| 6,020,126 A | 2/2000 | Carlsson et al. | |
| 6,063,604 A | 5/2000 | Wick et al. | |
| 6,087,133 A | 7/2000 | Dattagupta et al. | |
| 6,103,476 A | 8/2000 | Tyagi et al. | |
| 6,124,120 A | 9/2000 | Lizardi | |
| 6,214,587 B1 | 4/2001 | Dattagupta et al. | |
| 6,218,151 B1 | 4/2001 | Cleuziat et al. | |
| 6,238,868 B1 | 5/2001 | Carrino et al. | |
| 6,251,600 B1 | 6/2001 | Winger et al. | |
| 6,251,639 B1 * | 6/2001 | Kurn .................. 435/91.2 |
| 6,280,949 B1 | 8/2001 | Lizardi | |
| 6,309,833 B1 | 10/2001 | Edman et al. | |
| 6,326,173 B1 | 12/2001 | Edman et al. | |
| 6,410,278 B1 | 6/2002 | Notomi et al. | |
| 6,448,017 B1 | 9/2002 | Auerbach | |
| 6,461,817 B1 | 10/2002 | Alland et al. | |
| 6,977,148 B2 * | 12/2005 | Dean et al. ..................... 435/6 |
| 2001/0034048 A1 | 10/2001 | Kurn | |

(Continued)

FOREIGN PATENT DOCUMENTS

WO    WO 00/28082    5/2000

(Continued)

OTHER PUBLICATIONS

Shibata H et al. RNA-primed PCR. Genome Research, vol. 5, pp. 400-403, 1995.*

(Continued)

*Primary Examiner*—Suryaprabha Chunduru
(74) *Attorney, Agent, or Firm*—Casimir Jones, S.C.

(57) ABSTRACT

Methods, compositions and kits for amplifying a target sequence by strand displacement replication using strand-displacing primers. The method uses primers that have only ribonucleotides or purine ribonucleotides and at least one 2'-substituted pyrimidine-2'-deoxyribonucleotide.

64 Claims, 3 Drawing Sheets

U.S. PATENT DOCUMENTS

| | | |
|---|---|---|
| 2003/0017591 A1 | 1/2003 | Kurn |
| 2003/0087251 A1 | 5/2003 | Kurn |
| 2003/0186234 A1 | 10/2003 | Kurn |

FOREIGN PATENT DOCUMENTS

| | | |
|---|---|---|
| WO | WO 00/56877 | 9/2000 |
| WO | WO 02/16639 | 2/2002 |

OTHER PUBLICATIONS

Shibata, et al., "RNA-primed PCR", Genome Research, vol. 5, pp. 400-403 (1995).

* cited by examiner

Figur 2

Lane 1: Replication products with 100 picomoles of Riboprimers
Lane 2: Negative control without template
Lane 3: Negative control with DNA primer

METHODS FOR USING RIBOPRIMERS FOR STRAND DISPLACEMENT REPLICATION OF TARGET SEQUENCES

CROSS-REFERENCE TO RELATED APPLICATION

This application claims priority to U.S. Provisional Patent Application Ser. No. 60/428,013, filed Nov. 21, 2002. The entire disclosure of which is specifically incorporated herein by reference.

STATEMENT REGARDING FEDERALLY SPONSORED RESEARCH OR DEVELOPMENT

Not applicable.

FIELD OF THE INVENTION

The present invention relates generally to methods, compositions and kits for amplifying a target sequence by strand displacement replication. The method uses strand-displacing primers, having only ribonucleotides or purine ribonucleotides and at least one 2'-substituted pyrimidine-2'-deoxyribonucleotide.

BACKGROUND OF THE INVENTION

Methods for strand displacement amplification of linear templates are well known in the art. In general, methods for strand displacement amplification of linear templates use some kind of process to digest a sequence region at or near the 5'-end of one strand of a double-stranded DNA that has been synthesized using the other strand as a template in order to provide a complementary region for another primer to anneal to the template strand. Once annealed to the template, the primer is then "primer extended" by a DNA polymerase that has strand-displacing activity, thereby displacing the strand in front of the 3'-end of the replicating DNA. This process, which can be thought of as "liberating the primer binding site", is repeated over and over. Each round of liberating the primer binding site on the template, annealing of another primer and DNA synthesis results in release or "displacement" of the last-synthesized DNA strand.

By way of example, but not of limitation, methods for strand displacement amplification are disclosed in PCT Patent Publication Nos. WO 02/16639; WO 00/56877; and AU 00/29742 of Takara Shuzo Company; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al.; U.S. Pat. No. 6,251,639 and U.S. patent application Ser. 20010034048; 20030017591; 20030087251; and 20030186234 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi, all of which are incorporated herein by reference.

The methods disclosed in U.S. Pat. Nos. 5,523,204; 5,536,649; 5,624,825; 5,631,147; 5,648,211; 5,733,752; 5,744,311; 5,756,702; and 5,916,779 of Becton Dickinson and Company use a restriction enzyme to liberate the primer binding site.

The methods disclosed in U.S. Pat. Nos. 5,786,183; 6,087,133; and 6,214,587 of Gen-Probe, Inc. use multiple primers, typically with a 5'-flap, in the absence of a restriction enzyme to liberate the primer-binding sites. The methods disclosed in U.S. Pat. No. 6,063,604 of Wick et al., use primers designed to have a restriction endonuclease nick site to liberate the primer binding site from the template strand. The methods disclosed by Sagawa et al., in PCT Patent Publication No. WO 02/16639 and in PCT Patent Publications Nos. WO 00/56877 and AU 00/29742 use a composite primer having a 5'-portion comprising deoxyribonucleotides and a 3'-portion comprising ribonucleotides, and then use RNase H to liberate the primer-binding site at the 5'-end. The methods disclosed in U.S. Pat. No. 6,251,639 of Kurn use a composite primer having a 5'-portion comprising ribonucleotides and a 3'-portion comprising deoxyribonucleotides, and then use RNase H to liberate the primer-binding site at the 5'-end of the replicating DNA strand.

While all of these methods result in amplification of single-stranded DNA that is complementary to the template strand, still other methods and kits are needed that are less expensive and that permit easier design of assays for a variety of target sequences.

SUMMARY OF THE INVENTION

The present invention provides a method for amplifying a copy of a target sequence by repetitive strand-displacing DNA polymerization using a target sequence comprising a target nucleic acid as a template. More specifically, the present invention uses a DNA polymerase that is capable of strand-displacing DNA synthesis, i.e., wherein, a strand that is annealed to a template is displaced or released, beginning with its 5'-end portion, by the 3'-end of the DNA strand newly synthesized by the polymerase. The present method enables this repetitive copying of the template strand by use of novel primers and reaction conditions that permit, in repetitive succession, strand-displacing DNA polymerase-catalyzed primer extension synthesis of a copy of the target sequence, then digestion of at least a portion of the 5'-Riboprimer portion of the resulting primer extension product using a low level of an RNase H enzyme, then annealing of another primer, followed by strand-displacing primer extension again.

In one aspect the invention provides a method for amplifying a target nucleic acid sequence including a target nucleic acid by hybridizing a Riboprimer to a single stranded DNA template comprising the target nucleic acid sequence; optionally hybridizing a blocking oligo to a region of the template which is 5' with respect to hybridization of the Riboprimer to the template; extending the Riboprimer with DNA polymerase; and cleaving the annealed Riboprimer with an RNAse H enzyme such that another Riboprimer hybridizes to the template and repeats primer extension by strand displacement, whereby multiple copies of the complementary sequence of the target sequence are produced.

In another aspect the invention provides a method of producing a microarray, including amplifying a target nucleic acid sequence by the methods of the invention; and attaching the amplified products onto a solid substrate to make a microarray of the amplified products.

In another aspect the invention provides a method of producing a microarray, including amplifying a target nucleic acid sequence by the methods of the invention; and hybridizing the amplified products to a microarray of nuceic acid molecules immobilized on a surface of a solid phase.

In another aspect the invention provides a composition including a complex of a template strand; a Riboprimer; and a blocking oligo, wherein the blocking oligo affects cessation of DNA replication of a template by DNA polymerase.

In another aspect the invention provides a kit for amplification of a target nucleic acid sequence, including a Riboprimer and a blocking oligo, wherein the blocking oligo affects cessation of DNA replication of a template by DNA polymerase.

In another aspect the invention provides a method of generating multiple copies of a polynucleotide sequence complementary to an RNA sequence of interest, by (a) extending a first primer hybridized to a target RNA with an RNA-dependent DNA polymerase, wherein the first primer is a Riboprimer, whereby a complex comprising a first primer extension product and the target RNA is produced; (b) cleaving RNA in the complex of step (a) with an RNase H enzyme; (c) extending a second primer hybridized to the first primer extension product with a DNA-dependent DNA polymerase, whereby a second primer extension product is produced to form a complex of first and second primer extension products; (d) cleaving the Riboprimer in the complex of first and second primer extension products with an RNase H enzyme such that a Riboprimer hybridizes to the second primer extension product; and (e) extending the Riboprimer hybridized to the second primer extension product with a DNA-dependent DNA polymerase; whereby the first primer extension product is displaced, and whereby multiple copies of a polynucleotide sequence complementary to the RNA sequence of interest are generated.

Another aspect of the invention is the use of primers in strand displacement replication methods of the invention where the primers comprise only purine ribonucleotides and either only pyrimidine ribonucleotides or pyrimidine nucleotides wherein at least one pyrimidine nucleotide includes a pyrimidine 2'-deoxyribonucleotide having a non-canonical substituent (i.e. which is not a —H or —OH substituent) on the 2'-position of the deoxyribose sugar moiety. A suitable substituent on the 2'-position of the deoxyribose sugar moiety of a pyrimidine 2'-deoxyribonucleotide is a fluorine substituent.

In other aspects of the invention, the primers maybe both pyrimidine 2'-deoxyribonucleotides including a 2'-fluoro-2'-deoxyribonucleotide, conferring resistance to many common RNase A-type ribonucleases (which specifically cut RNA at pyrimidine nucleotides).

In still other aspects of the invention, one of the primers may include a pyrimidine nucleotide having a canonical ribonucleotide and the other a pyrimidine nucleotide having a pyrimidine 2'-deoxyribonucleotide with a non-canonical substituent on the 2'-position of the deoxyribose sugar moiety.

In still other aspects, some or all of one of the pyrimidine nucleotides in a reaction comprise a 2'-deoxyribonucleotide having an amino, an azido, a methoxy, or another non-canonical substituent on the 2'-position of the deoxyribose sugar moiety.

Thus, in contrast to other methods of the art, the strand displacement replication methods of the present invention use primers comprising ribonucleotides or primers comprising purine ribonucleotides and at least one 2'-substituted pyrimidine deoxyribonucleotide in order to amplify a target sequence. The primers used in strand displacement methods and kits of the present invention can be obtained from commercial sources at reasonable cost or synthesized inexpensively in high yield using a simple and rapid in vitro transcription reaction.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
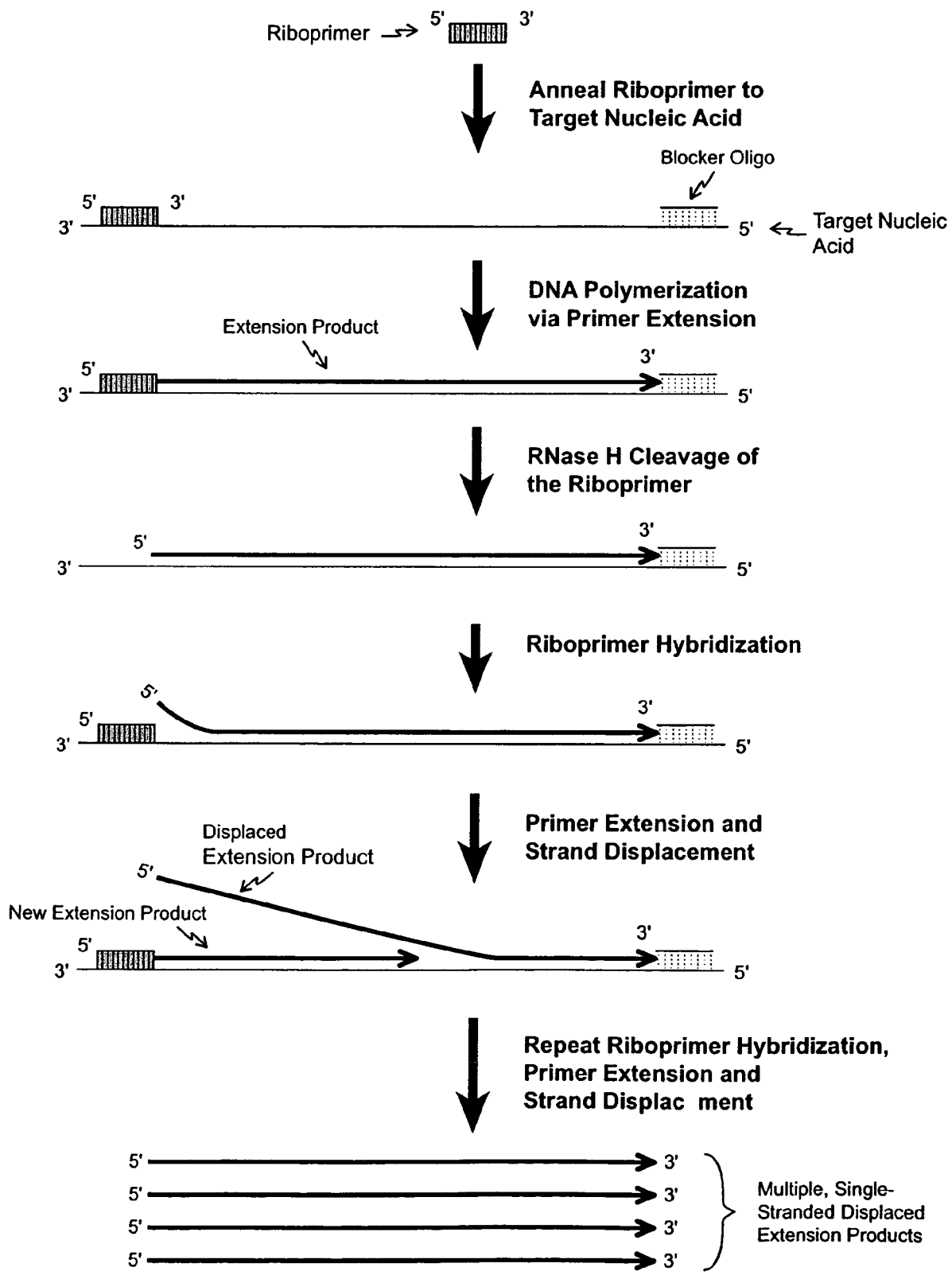
FIG. 1. Schematic of a basic embodiment of the invention using a Riboprimer for strand displacement replication of a target sequence.
Figure 2:
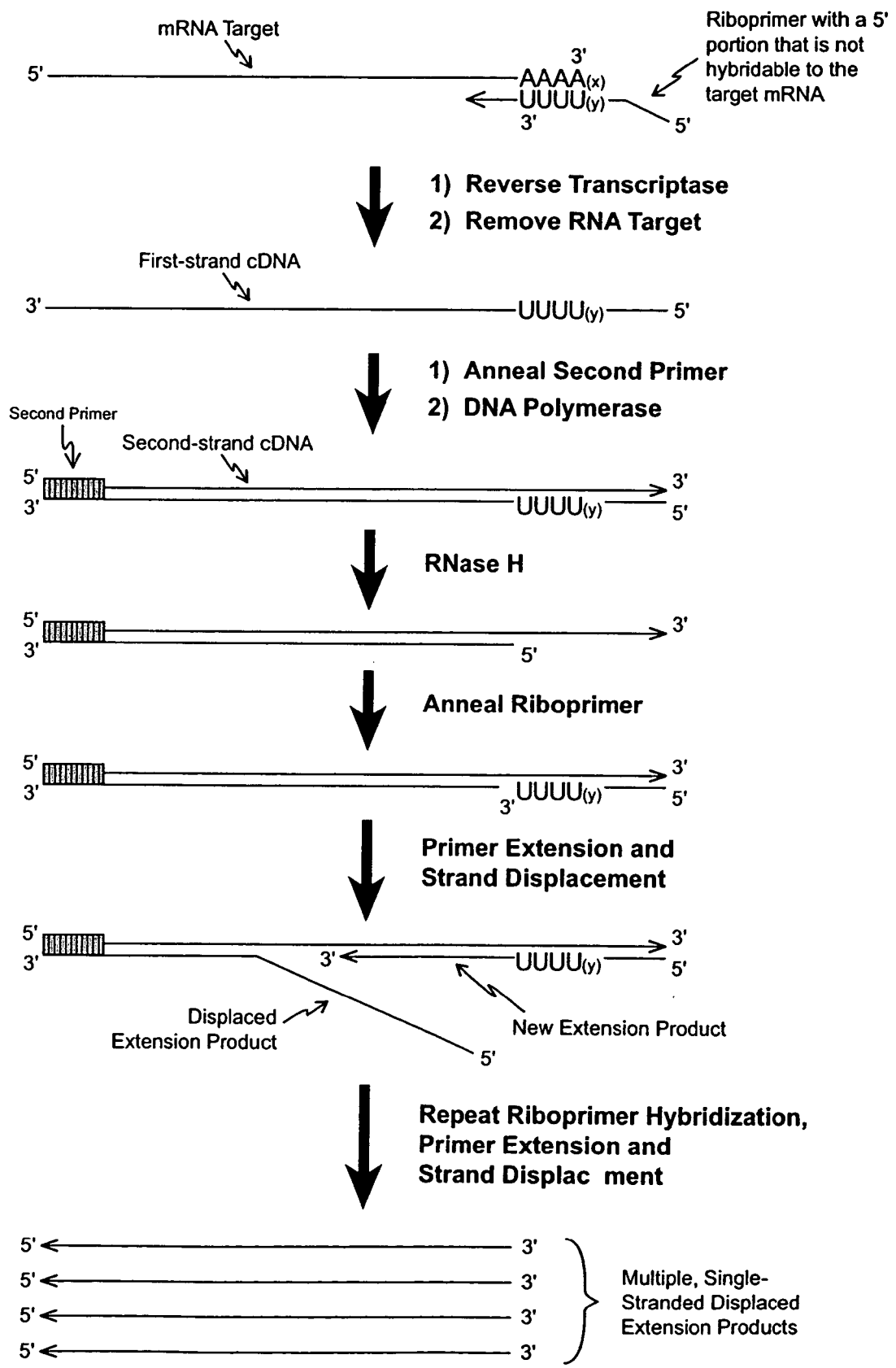
FIG. 2. Schematic of an embodiment of the invention that uses a Riboprimer having a 5'-portion that is not complementary to the target sequence as a primer for first-strand primer extension of a target sequence. Then, synthesis of second-strand DNA takes place by a DNA polymerase or reverse transcriptase under polymerization conditions, whereby the non-complementary portion of the Riboprimer is "copied". The Riboprimer therefore has a longer region of complementarity for annealing and the $T_m$ of the Riboprimer/second-strand DNA complex is higher. If the first-strand DNA in this example is complementary to a target nucleic acid in the sample (e.g., an mRNA target), the strand displacement replication reaction shown amplifies the second-strand DNA, thereby synthesizing "anti-sense" DNA.

The present invention relates to a method for amplifying a copy of a target sequence by repetitive strand-displacing DNA polymerization using a target sequence comprising a target nucleic acid as a template. More specifically, the present invention uses a DNA polymerase that is capable of strand-displacing DNA synthesis, i.e., wherein, a strand that is annealed to a template is displaced or released, beginning with its 5'-end portion, by the 3'-end of the DNA strand newly synthesized by the polymerase. The present method enables this repetitive copying of the template strand by use of novel primers and reaction conditions that permit, in repetitive succession, strand-displacing DNA polymerase-catalyzed primer extension synthesis of a copy of the target sequence, then digestion of at least a portion of the 5'-Riboprimer portion of the resulting primer extension product using a low level of an RNase H enzyme, then annealing of another primer, followed by strand-displacing primer extension again.

Thus, in contrast to the methods for strand displacement amplification in the art which use a chimeric primer consisting of a 5'-portion or a 3'-portion comprising only ribonucleotides or only deoxyribonucleotides, the present invention uses only purine ribonucleotides in both the 5'-portion and the 3'-portion. Similarly, the pyrimidine nucleotides used in the present invention whether they comprise ribonucleotides or a 2'-deoxyribonucleotides having a non-canonical 2'-substituent, can be in both the 5'-portion or the 3'-portion of the primer.

Definitions

Amplifying a Nucleic Acid/Amplification Reaction/Amplification Product

The term "amplifying a nucleic acid" herein means increasing the number of copies of a target nucleic acid sequence or its complement. The nucleic acid that is amplified can be DNA or RNA or a mixture of DNA and RNA, including modified DNA and/or RNA. The terms "amplifying RNA" or "amplifying DNA" mean, either, increasing the number of copies of target nucleic acid having a sequence that is identical to a sequence in the starting RNA or DNA, or increasing the number of copies of a nucleic acid having a sequence that is complementary to or homologous to a sequence in the starting RNA or DNA. The products resulting from amplification of a nucleic acid molecule or molecules (i.e., "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification).

Template

A "template" is a nucleic acid molecule that is being copied by a nucleic acid polymerase. The synthesized copy is complementary to the template. Both RNA and DNA are always synthesized in the 5'-to-3' direction and the two strands of a nucleic acid duplex always are aligned so that the 5' ends of the two strands are at opposite ends of the duplex (and, by necessity, so then are the 3' ends). In general, DNA polymerases, including both DNA-dependent (i.e, having a DNA template) and RNA-dependent (i.e., having an RNA template, which enzyme is also called a "reverse transcriptase") DNA polymerases, require a primer for synthesis of DNA.

The term "template" is used in different contexts related to the present invention. In one context, a target nucleic acid comprising RNA or DNA can be a "template" for obtaining a ssDNA comprising a target sequence by primer extension of a suitable DNA primer using a reverse transcriptase or DNA polymerase. In another context, a method of the present invention uses a ssDNA comprising the target sequence as a "template" for primer extension of a Riboprimer of the invention using a DNA polymerase. In some embodiments wherein the target nucleic acid comprises DNA, the ssDNA comprising the target sequence can be used directly as an amplification template for primer extension using a Riboprimer of the invention.

The terms "3'-of" and "5'-of" are used herein to refer to the position of a particular nucleotide, nucleic acid sequence, gene or genetic element within a nucleic acid or polynucleotide or oligonucleotide relative to other nucleotides, sequences, genes or genetic elements. Those with knowledge in the art will understand these terms in the context of nucleic acid chemistry and structure, particularly related to the 3'- and 5'-positions of sugar moieties of canonical nucleic acid nucleotides, and in the context of enzymatic synthesis of nucleic acids in a 5'-to-3' direction. Those with knowledge in the art will understand that, if a first nucleic acid sequence is 3'-of a second sequence on one strand, the complement of the first sequence will be 5'-of the complement of the second sequence on the complementary strand.

Primer

A "primer" is an oligonucleotide, generally with a free 3'-OH group, that is complementary to a template and which "binds" (or "complexes" or "anneals" or "hybridizes"), by hydrogen bonding and other molecular forces, to the template to give a primer/template complex for initiation of synthesis by a DNA polymerase, and which is extended (i.e., "primer extended") by nucleotides being covalently linked its 3'-end with bases complementary to those at the template in the process of DNA synthesis. The result is a primer extension product. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer.

Like templates, primers are used in different contexts related to the present invention. The primers are different in each context.

In one context, the primer is used "to prime" primer extension on a template comprising a target nucleic acid in order to obtain a ssDNA comprising a target sequence, but not to prime strand-displacing amplification using a method of the invention. In this context, the primer usually, but not necessarily, comprises deoxyribonucleotides rather than ribonucleotides. If a primer comprising ribonucleotides is used in this context, then the ribonucleotides are removed from the resulting ssDNA comprising the target sequence prior to use of the ssDNA as a template for amplification using a Riboprimer in a method of the invention.

In another context, a Riboprimer is used in methods of the present invention in order to prime strand-displacing primer extension using a ssDNA comprising a target sequence as a template.

Plus/Minus Strand(s)

Discussions of nucleic acid synthesis are simplified and clarified by adopting terms to name the two complementary strands of a nucleic acid duplex. Traditionally, the strand encoding the sequences used to produce proteins or structural RNAs is designated as the "plus" or "sense" strand, and its complement is designated as the "minus" or "anti-sense" strand. It is now known that in many cases, both strands are functional, and the assignment of the designation "plus" to one and "minus" to the other must then be arbitrary. Nevertheless, the terms are useful for designating the sequence orientation of nucleic acids or for designating the specific mRNA sequences transcribed and/or present in a particular cell, tissue, or sample, and are employed herein for that purpose.

Hybridize/Anneal/Complex/Hybridization/Annealing

The terms "to complex" or "to hybridize" or "to anneal" and "complexing" or "hybridization" or "annealing" refer to the formation of "complexes" or "hybrids" between nucleic acid sequences that are sufficiently complementary to bind to each other via Watson-Crick base pairing. Where a primer "hybridizes" or "anneals" with a template, such complexes (or hybrids) are sufficiently stable to serve the priming function required by the DNA polymerase to initiate DNA synthesis.

Nucleic Acids and Polynucleotides of the Invention

A "nucleic acid" or "polynucleotide" of the invention is a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5' of" or "upstream of," or the "5' nucleotide" and the nucleotide that is linked to the 3'-position of the 5' or upstream nucleotide is referred to as "3' of," or "downstream of," or the "3' nucleotide." The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common "nucleic acid bases" (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. Those in the art commonly think of a small polynucleotide as an "oligonucleotide." The term "oligonucleotide" as used herein is defined as a molecule comprised of two or more deoxyribonucleotides or ribonucleotides, preferably about 10 to 200 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the melting temperature ($T_m$); (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface.

In order to accomplish the goals of the invention, there is no limit to the composition of the nucleic acids or polynucleotides of the invention, including any detection probes, such as, but not limited to molecular beacons (U.S. Pat. Nos. 5,925,517 and 6,103,476 of Tyagi et al., and 6,461,817 of Alland et al., all of which are incorporated herein by reference); capture probes, oligonucleotides, or other nucleic acids used or detected in the assays or methods, so long as each of the nucleic acid functions for its intended use. By way of example, but not of limitation, the nucleic acid bases in the mononucleotides may comprise guanine, adenine, uracil, thymine, or cytidine, or alternatively, one or more of the nucleic acid bases may comprise xanthine, allyamino-uracil, hypoxanthine, 2-aminoadenine, 6-methyl and other alkyl adenines, 2-propyl and other alkyl adenines, 5-halouracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-aminoadenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8-substituted adenines and 8-halo guanines, 8-amino-guanine, 8-thiol guanine, 8-thiolalkyl guanines, 8-hydroxyl guanine and other 8-substituted guanines, other aza and deaza uracils, other aza and deaza thymidines, other aza and deaza cytosine, aza and deaza adenines, aza and deaza guanines or 5-trifluoromethyl uracil and 5-trifluorocytosine. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show the broad range of bases which may be used for a particular purpose in a method.

In some embodiments of the invention, a molecule comprising a "peptide nucleic acid" (PNA) or a molecule comprising both a nucleic acid and a PNA, as described in U.S. Pat. Nos. 5,539,082; 5,641,625; 5,700,922; 5,705,333; 5,714,331; 5,719,262; 5,736,336; 5,773,571; 5,786,461; 5,817,811; 5,977,296; 5,986,053; 6,015,887; and 6,020,126 (and references therein), can also be used. In general, a PNA molecule is a nucleic acid analog consisting of a backbone comprising, for example, N-(2-aminoethyl)glycine units, to each of which a nucleic acid base is linked through a suitable linker, such as, but not limited to an aza, amido, ureido, or methylene carbonyl linker. The nucleic acid bases in PNA molecules bind complementary single-stranded DNA or RNA according to Watson-Crick base-pairing rules. However, the $T_m$'s for PNA/DNA or PNA/RNA duplexes or hybrids are higher than the $T_m$'s for DNA/DNA, DNA/RNA, or RNA/RNA duplexes. PNA can provide tighter binding and greater binding stability than a nucleic acid of similar base sequence (e.g., see U.S. Pat. No. 5,985,563). Also, since PNA is not naturally occurring, PNA molecules are highly resistant to protease and nuclease activity. PNA can be prepared according to methods know in the art, such as, but not limited to, methods described in the above-mentioned patents, and references therein.

When a molecule comprising both a nucleic acid and a peptide nucleic acid (PNA) is used in the invention, modified bases can be used in one or both parts. For example, binding affinity can be increased by the use of certain modified bases in both the nucleotide subunits that make up the 2'-deoxyoligonucleotides of the invention and in the peptide nucleic acid subunits. Such modified bases may include 5-propynylpyrimidines, 6-azapyrimidines, and N-2, N-6 and O-6 substituted purines including 2-aminopropyladenine. Other modified pyrimidine and purine base are also expected to increase the binding affinity of macromolecules to a complementary strand of nucleic acid.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose, or 2'-O-methyl-ribose, or 2'-amino-2'-deoxyribose, or 2'-azido-2'-deoxyribose.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases.

When two different, non-overlapping polynucleotides or oligonucleotides hybridize or anneal to different regions of the same linear complementary nucleic acid sequence, and the 3'-end of one polynucleotide or oligonucleotide points towards the 5'-end of the other, the former may be called the "upstream" polynucleotide or oligonucleotide and the latter the "downstream" polynucleotide or oligonucleotide.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

Methods for Making Nucleic Acids and Polynucleotides

A variety of methods are known in the art for making nucleic acids that have a particular sequence or that contain particular nucleic acid bases, sugars, internucleoside linkages, chemical moieties, and other compositions and characteristics. Any one or any combination of these methods can be used to make a nucleic acid, polynucleotide, or oligonucleotide for the present invention. These methods include, but are not limited to:

(1) chemical synthesis (usually, but not always, using a nucleic acid synthesizer instrument);

(2) post-synthesis chemical modification or derivatization;

(3) cloning of a naturally occurring or synthetic nucleic acid in a nucleic acid cloning vector (e.g., see Sambrook, et al., Molecular Cloning: A Laboratory Approach $2^{nd}$ ed., Cold Spring Harbor Laboratory Press, 1989) such as, but not limited to a plasmid, bacteriophage (e.g., m13 or lamba), phagemid, cosmid, fosmid, YAC, or BAC cloning vector, including vectors for producing single-stranded DNA;

(4) primer extension using an enzyme with DNA template-dependent DNA polymerase activity, such as, but not limited to, Klenow, T4, T7, rBst, Taq, Tfl, Tth or phi29 DNA polymerases (U.S. Pat. Nos. 5,576,204 and 5,001,050 to Blanco et al., incorporated herein by reference; phi29 is available under the trademark name RepliPHI™ from Epicentre Technologies, Madison, Wis., USA), including mutated, truncated (e.g., exo-minus), or chemically-modified forms of such enzymes;

(5) PCR (e.g., see Dieffenbach, C. W., and Dveksler, eds., PCR Primer: A Laboratory Manual, 1995, Cold Spring Harbor Laboratory Press, Cold Spring Harbor, N.Y.);

(6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), or *Thermus thermophilus* (Tth);

(7) in vitro transcription using an enzyme with RNA polymerase activity, such as, but not limited to, SP6, T3, or T7 RNA polymerase, Tth RNA polymerase, *E. coli* RNA polymerase, or SP6 or T7 R&DNA™ Polymerase (EPICENTRE Technologies, Madison, Wis., USA), or another enzyme;

(8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids;

(9) use of polynucleotide phosphorylases to make new randomized nucleic acids;

(10) other compositions, such as, but not limited to, a ribozyme ligase to join RNA molecules; and/or

(11) any combination of any of the above or other techniques known in the art. Oligonucleotides and polynucleotides, including chimeric (i.e., composite) molecules and oligonucleotides with modified bases, sugars, or internucleoside linkages are commercially available (e.g., from TriLink Biotechnologies, San Diego, Calif., USA or Integrated DNA Technologies, Coralville, Iowa).

Target Nucleic Acids and Target Nucleic Acid Sequences

A "target nucleic acid" has a "target sequence" to be amplified, and may be either single-stranded or double-stranded and may include other sequences besides the target sequence which may not be amplified. A target nucleic acid is sometimes referred to more specifically by the type of nucleic acid. By way of example, but not of limitation, a target nucleic acid can be a "target RNA" or an "RNA target," or a "target mRNA," or a "target DNA" or a "DNA target." Similarly, the target sequence can be referred to as "a target RNA sequence" or a "RNA target sequence", or as a "target mRNA sequence" or a "target DNA sequence," or the like. In some embodiments, the target sequence comprises one or more entire target nucleic acids, such as, but not limited to, mRNA target nucleic acids in a particular cell. In other embodiments, the target sequence comprises only a portion of one or more nucleic acid molecules. The term "target sequence" refers to the particular nucleotide sequence of the target nucleic acid(s) that is/are to be amplified. The "target sequence" includes the complexing sequences to which the oligonucleotides (primers and/or splice templates) complex during the processes of the present invention, including "tail" sequences which are added by means including, but not limited to, non-templated addition of dCMP residues to first-strand cDNA by reverse transcriptase pausing at cap structures of mRNA (in the presence or absence of manganese cations) and/or controlled ribonucleotide tailing using TdT. When the target nucleic acid is originally single-stranded, the term "target sequence" is also meant to refer to the sequence complementary to the "target sequence." When the "target nucleic acid" is originally double-stranded, the term "target sequence" refers to both the (+) and (−) strands. The target sequence may be known or not known, in terms of its actual sequence. In some instances, the terms "target sequence," "target nucleic acid," "target polynucleotide," and variations thereof, are used interchangeably.

A target nucleic acid, comprising a target sequence to be amplified, includes nucleic acids from any biological source, whether living or dead, in purified or unpurified form. Target nucleic acids can be any single-stranded DNA (ssDNA) or double-stranded DNA (dsDNA), including, but not limited to mitochondrial DNA, chloroplast DNA, chromosomes, plasmids or other episomes, the genomes of bacteria, yeasts, viruses, viroids, mycoplasma, molds, or other microorganisms, or genomes of fungi, plants, animals, or humans, or target nucleic acids can be any RNA, including, but not limited to tRNA, mRNA, rRNA, mitochondrial RNA, chloroplast RNA, or target nucleic acids can be mixtures of DNA and RNA, including, but not limited to, mixtures of the above nucleic acids or fragments thereof, or DNA-RNA hybrids. The target nucleic acid can be only a minor fraction of a complex mixture such as a biological sample and can be obtained from various biological materials by procedures known in the art. Methods for purification of a target nucleic, if further purification is necessary, are also known in the art that can be used to obtain a target nucleic acid for use in a method of the invention.

A. General Methods for Obtaining a Target Sequence

An initial step in obtaining a target nucleic acid sequence is rendering the target nucleic acid single-stranded. If the target nucleic acid is a dsDNA, the initial step is target denaturation. The denaturation step may be thermal denaturation or any other method known in the art, such as alkali treatment.

In some embodiments of the invention in which the target nucleic acid in a sample is DNA, the ssDNA target sequence comprises either ssDNA that is present in a biological sample or ssDNA that is obtained by denaturation of dsDNA in the sample.

In other embodiments, the ssDNA target sequence comprises ssDNA that is obtained as a result of a "primer extension reaction," meaning an in vitro or in vivo DNA polymerization reaction using either ssDNA or denatured dsDNA that is present in the sample as a template and an oligonucleotide as a primer under DNA polymerization reaction conditions.

In some embodiments the target nucleic acid in the sample or the primer extension product, or both, are made into smaller DNA fragments by methods known in the art in order to generate a DNA target sequence for use in the methods of the invention.

In some embodiments using samples containing DNA target nucleic acids, a ssDNA target sequence is obtained by a strand displacement reaction using a strand displacement method of the present invention. In other embodiments, a ssDNA target sequence is obtained using another strand displacement method, such as but not limited to the methods described in PCT Patent Publication Nos. WO 02/16639; WO 00/56877; and AU 00/29742 of Takara Shuzo Company, Kyoto, Japan; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al.; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi, all of which are incorporated herein by reference. In still other embodiments the ssDNA target sequence is obtained from a rolling circle replication reaction. The 3'-end of the DNA target sequence can be defined, if it need be defined, by using any suitable method known in the art, such as, but not limited to a method discussed herein below.

If the target nucleic acid is RNA, the initial step for obtaining a target sequence can be the synthesis of a single-stranded cDNA. In general, "cDNA" refers herein to "complementary DNA" that is synthesized by primer extension by a DNA polymerase, including, but not limited to, an RNA-dependent DNA polymerase, using at least a portion of a nucleic acid as a template, and which cDNA is "homologous to" or "base pairs with" or "complexes with" at least a portion of the nucleic acid template. In some embodiments of the invention, a target sequence comprises cDNA that is synthesized by reverse transcription primer extension by an RNA-dependent DNA polymerase (i.e., "reverse transcriptase") using a target nucleic acid comprising messenger RNA (mRNA) obtained from a biological sample as a template, which cDNA is homologous to the mRNA. In other embodiments, a target sequence comprising cDNA is obtained by reverse transcriptase primer extension using an RNA target that is not mRNA as a template, or by primer extension using a single-stranded DNA target or one strand of a double-stranded DNA target as a template.

Techniques for the synthesis of cDNA from RNA are known in the art as described herein. Thus, in some embodiments of the invention, the target nucleic acid is RNA and the ssDNA target sequence comprises first-strand cDNA obtained by reverse transcription of the RNA target, meaning an in vitro reaction that utilizes an RNA present in a sample as a template and a nucleic acid oligonucleotide that is complementary to at least a portion of a sequence of the RNA template as a primer in order to synthesize ssDNA using an RNA-dependent DNA polymerase (i.e., reverse transcriptase) under reaction conditions.

An "RNA-dependent DNA polymerase" or "reverse transcriptase" is an enzyme that synthesizes a complementary DNA copy ("cDNA") from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates. Examples of reverse transcriptases that can be used in methods of the present invention include, but are not limited to, AMV reverse transcriptase, MMLV reverse transcriptase, Tth DNA polymerase, rBst DNA polymerase large fragment, also called IsoTherm™ DNA Polymerase (EPICENTRE Technologies, Madison, Wis., USA), and BcaBEST™ DNA polymerase (Takara Shuzo Co, Kyoto, Japan). In some cases, a mutant form of a reverse transcriptase, such as, but not limited to, an AMV or MMLV reverse transcriptase that lacks RNase H activity is suitable.

In some embodiments, a first-strand cDNA for use in methods of the invention is synthesized in situ in cells or tissue in a tissue section using methods similar to those described in U.S. Pat. Nos. 5,168,038; 5,021,335; and 5,514,545, which are incorporated herein by reference. Thus, the first-strand cDNA is synthesized by contacting the cells or tissue in the tissue section under hybridizing conditions with a primer, wherein the primer hybridizes to one or more target sequences in the cell or tissue, and then contacting the primer-mRNA complex with a reverse transcriptase under reverse transcription reaction conditions.

An oligonucleotide primer for synthesis of cDNA using an RNA target as a template can be complementary to a specific known sequence in the RNA target in a sample, or the oligonucleotide primer(s) can comprise a mixture of all possible or many possible sequences, such as, but not limited to, random hexamer primers. Random primers can be made by including nucleotide reagents that are complementary to each of the four canonical bases (i.e., all four nucleotides) during the chemical synthesis of each nucleotide position of the oligonucleotide that is complementary to the target sequence. In embodiments of the invention using samples containing mRNA targets, the ssDNA target sequence comprises first-strand cDNA that is made by reverse transcription of the mRNA using an oligonucleotide primer comprising either a specific sequence which is complementary to a known sequence of a specific mRNA or, if the mRNA has a poly(A) tail at its 3'-end, an oligo(dU) primer or an oligo(dU) anchor primer.

B. Methods for Defining the 5'- and 3'-Ends of Target Sequences That Comprise Only a Portion of a Larger RNA or DNA Target Nucleic Acid When a method of the invention is used to amplify the complete sequence(s) of one or a multitude of nucleic acid molecules, such as, but not limited to, the complete sequences of mRNA molecules (excluding the cap structure) in a sample, it is not necessary to devise additional methods to define the 5'- and 3'-ends of the sequences. However, if a method of the invention is used to amplify a target sequence that comprises only a portion of a larger RNA or DNA nucleic acid in a sample, then additional methods are needed to delimit the target sequence that comprises the template sequence that is amplified.

There are two general approaches to delimiting the ends of the target sequence that is amplified. In the first direct approach, methods are used to determine the size and end sequences of a target nucleic acid molecule or molecules present in the sample itself. In the second indirect approach, instead of changing the size and end sequences of the target nucleic acid molecules present in a sample, methods are used to determine the size and end sequences of one or more first-strand cDNA molecules that is synthesesized by reverse transcription or primer extension, respectively, of RNA or of at least one strand of DNA in a sample.

With respect to the direct approach, a number of methods are known in the art for cleaving a nucleic acid molecule at or near a specific sequence, and any of the methods which delimit the size and end sequences of a target nucleic acid for an application of the present invention can be used. By way of example, but not of limitation, a DNA in a sample comprising a dsDNA molecule or a ssDNA molecule to which an appropriate complementary DNA oligo is annealed can be digested with a restriction endonuclease, provided a restriction site that would provide a suitable 5'-end and/or 3'-end sequence is present. Alternatively, one or more DNA oligonucleotides having a double-stranded segment that contains a FokI restriction enzyme site and a single-stranded segment that binds to the desired cleavage site on a first-strand cDNA can be used. As is well known in the art, this type of oligonucleotide can be used with the restriction enzyme FokI to cut a single-stranded DNA at almost any desired sequence (Szybalski, W., Gene, 40: 169-173, 1985; Podhajska A. J. and Szybalski W., Gene 40:175, 1985, incorporated herein by reference).

By way of further example, but not of limitation, a ssRNA target nucleic acid present in a sample can be cleaved using a ribonuclease H in regions to which complementary oligonucleotides comprising at least three-to-four deoxyribonucleotides, and preferably four to ten deoxyribonucleotides, are annealed. Alternatively, a linear DNA oligonucleotide can be annealed to an RNA in a sample at a location that encodes a recognition site of a restriction enzyme that can cut RNA:DNA heteroduplexes. Cutting the target RNA:DNA oligo with the enzyme will then generate a defined end. Alternatively, an RNA or DNA oligo or polynucleotide with a sequence complementary to the region of an RNA target sequence that is intended to become a substrate for amplification can be annealed to the RNA and the sequences of the RNA to which the oligo or polynucleotide is not annealed can be digested using a single-strand-specific ribonuclease, such as RNase A or RNase T1. Still further, either RNA or DNA nucleic acids of known sequence can be cleaved at specific sites using a 5'-nuclease or Cleavase® enzyme and specific oligonucleotides, as described by Kwiatkowski, et al., (Molecular Diagnosis, 4: 353-364, 1999) and in U.S. Pat. No. 6,001,567 and related patents assigned to Third Wave Technologies (Madison, Wis., USA), which are incorporated herein by reference.

In general, with respect to the second indirect approach, the 5'-end of the primer that is used for reverse transcription of RNA in a sample or for primer extension of at least one strand of DNA in a sample defines the 5'-end of the first-strand cDNA target sequence that is amplified in the methods of the present invention. Thus, a sample target nucleic acid that is reverse transcribed or primer extended to make a first-strand cDNA target sequence need not have a defined 3'-end.

In order to generate a defined 3'-end on a first-strand cDNA (i.e., corresponding to the 5'-end of the target sequence), a number of methods known in the art may be used, all of which are envisioned as methods of the present invention. By way of example, but not of limitation, if a specific sequence is present in the first-strand cDNA that corresponds to a restriction endonuclease site that would provide a suitable 3'-end sequence, a complementary DNA oligo can be annealed to this sequence and the site can be cleaved with the restriction enzyme. The DNA oligo may optionally have a 2',3'-dideoxy end, a 2'-amino end, or another end so that it cannot be extended by a DNA polymerase. Alternatively, the 3'-end can be defined using a DNA oligonucleotide having a double-stranded segment that contains a FokI restriction enzyme site and a single-stranded segment that binds to the desired cleavage site on a first-strand cDNA (Szybalski, W., Gene, 40: 169-173, 1985; Podhajska A. J. and Szybalski W., Gene 40:175, 1985), as discussed previously. Still further, a 5'-nuclease can be used to cleave a first-strand cDNA at a defined 3'-end as discussed above.

In addition to the above methods, the 3'-end of a first-strand cDNA can also be limited by other methods. A preferred method of the invention is to use a "blocking oligo" or a "blocker sequence," as disclosed by Laney, et al., in U.S. Pat. No. 5,679,512, and by Kurn in U.S. Pat. No. 6,251,639, both of which are incorporated herein by reference. The "blocker sequence" or "blocker oligo" is a polynucleotide, which is usually a synthetic polynucleotide that is single-stranded and comprises a sequence that is hybridizable, and preferably complementary, to a segment of target nucleic acid, wherein the blocking oligo anneals to the target nucleic acid so as to block further primer extension of the 3'-end of first-strand cDNA at a desired position. Some embodiments of the processes of the strand displacement replication methods of the present invention use a blocking oligo. The blocking oligo comprises nucleotides that bind to the target nucleic acid with an affinity, preferably a high affinity, such that the blocker sequence resists displacement by DNA polymerase in the course of primer extension, in preferably more than about 30%, more preferably more than about 50%, even more preferably more than about 75%, and most preferably more than about 90%, of primer extension events. The length and composition of the blocker polynucleotide should be such that excessive random non-specific hybridization is avoided under the conditions of the methods of the present invention. The length of the blocker polynucleotide is preferably from about 3 to about 30 nucleotides, more preferably from about 5 to about 25 nucleotides, even more preferably from about 8 to about 20 nucleotides, and most preferably from about 10 to about 15 nucleotides. In other embodiments, the blocker polynucleotide is at least about any of the following: 3, 5, 8, 10, 15; and less than about any of the following: 20, 25, 30, 35. It is understood that the length can be greater or less as appropriate under the reaction conditions of the methods of this invention. The complementarity of the blocker polynucleotide is preferably at least about 25%, more preferably at least about 50%, even more preferably at least about 75%, and most preferably at least about 90%, to its intended binding sequence on the target nucleic acid. In some embodiments, the blocker sequence that hybridizes to a DNA target nucleic acid is attached to the DNA such that displacement of the blocker sequence by the polymerase that effects primer extension is substantially, or at least sufficiently, inhibited.

Suitable methods for achieving such attachment include techniques known in the art, such as using a cytosine analog that contains a G-clamp heterocycle modification as described by Flanagan et al., (Proc. Natl. Acad. Sci. USA 96: 3513-3518, 1999); and locked nucleic acids as described, e.g., by Kumar et al., (Bioorg. Med. Chem Lett., 8: 2219-2222, 1998; and by Wahlestedt et al., (Proc. Natl. Acad. Sci. USA 97: 5633-5638, 2000), all of which are incorporated herein by reference. Other suitable methods include using, where appropriate, sequences with a high GC content and/or cross-linking. Any of these methods for obtaining enhanced attachment may be used alone or in combination. Alternatively, a molecule comprising a peptide nucleic acid (PNA) can be used.

Still further, another method that can be used to limit the 3'-end of a first-strand cDNA is to use a thermocycler with short DNA synthesis elongation cycles during reverse transcription or primer extension to synthesize first-strand cDNA. The length of the product can be somewhat controlled by the length of the DNA synthesis cycle. Conditions can be determined to define an approximate chain length of first-strand cDNA by controlling the temperature and time interval of DNA synthesis before denaturing the growing first-strand cDNA from the template by raising the temperature.

Further, the 3'-end of a first-strand cDNA that is to become the template sequence for a strand displacement replication reaction can be defined by first amplifying the target nucleic acid sequence using another amplification method that delimits the end sequence. By way of example, but not of limitation, it can be prepared using PCR, RT-PCR, NASBA, TMA, 3SR, Ligation Chain Reaction (LCR), Linked Linear Amplification (BioRad), SDA, RCA, ICAN™ (Takara: Sagawa et al., in PCT Patent Publication No. WO 02/16639; and in PCT Patent Publications Nos. WO 00/56877 and AU 00/29742); or a strand-displacement method of Kurn (U.S. Pat. No. 6,251, 639), all of which are incorporated herein by reference.

If a 3'-end of a target sequence need not be at an exact location, and can be random or imprecise, which is the case in some embodiments of the invention, there are a number of other methods that can be used for making smaller fragments of a DNA molecule, whether for a target nucleic acid, a target sequence, or otherwise. By way of example, but not of limitation, a target nucleic acid can be fragmented by physical means, such as by movement in and out of a syringe needle or other orifice or by sonication, preferably with subsequent end repair, such as using a T4 DNA polymerase or a kit, such as the End-It™ DNA End Repair Kit (EPICENTRE Technologies, Madison, Wis., USA).

Still another method that can be used is to incorporate dUMP randomly into the first-strand cDNA during reverse transcription or primer extension by using dUTP in place of a portion of the TTP in the reaction. The dUMP will be incorporated randomly in place of TMP at a frequency based on the ratio of dUTP to TTP. Then, the first-strand cDNA can be cleaved at sites of dUMP incorporation by treatment (e.g., see U.S. Pat. No. 6,048,696, incorporated herein by reference) with uracil-N-glycosylase (UNG) and endonuclease IV (endo IV), which are available from EPICENTRE Technologies (Madison, Wis., USA). UNG hydrolyzes the N-glycosidic bond between the deoxyribose sugar and uracil in single- and double-stranded DNA that contains uracil in place of thymidine. It has no activity on uracil residues in RNA or on dUTP. Endo IV cleaves the phosphodiester linkage at the basic site. It may be useful to use a thermolabile UNG (e.g., HK™-UNG from EPICENTRE Technologies, Madison, Wis., USA) for some applications. (Also, incorporation of dUMP at specific sites within a synthetic oligonucleotide or, for example, within a promoter primer of the invention between the 3'-target-sequence-complementary portion and the promoter sequence, introduces specific cleavage sites which can be used at any time to cleave a resulting nucleic acid which contains the site by treatment with UNG and endo IV.)

Still further, in some cases, the 3'-end of a first-strand cDNA can be defined by treatment with exonuclease III (Henikoff, S., Gene, 28: 351, 1984). In still other cases, the 3'-end of a first-strand cDNA that is annealed to a DNA target nucleic acid can be incubated with T4 DNA polymerase or unmodified T7 DNA polymerase in the absence or the presence of dNTPs in the reaction (2002 EPICENTRE Catalog, pp. 129 and 130); these enzymes have the 3'-to-5' exonuclease activity in the absence of dNTPs, but the polymerase activity predominates in the presence of dNTPs. These are only some of the methods that can be used to define the 3'-ends of a first-strand cDNA, and the invention is not limited to these methods, which are presented only as examples.

General Methods of the Invention

The following are general methods of the invention which are further characterized and supported by the detailed descriptions hereinbelow.

In one embodiment, the invention provides a method for amplifying a target nucleic acid sequence comprising a target nucleic acid, the method comprising:

(a) hybridizing a Riboprimer to a single-stranded DNA template comprising the target nucleic acid sequence;

(b) optionally, hybridizing a blocking oligo to a region of the template which is 5' with respect to hybridization of the Riboprimer to the template;

(c) extending the Riboprimer with DNA polymerase; and (d) cleaving the annealed Riboprimer with an enzyme that cleaves RNA from an RNA/DNA hybrid such that another Riboprimer hybridizes to the template and repeats primer extension by strand displacement, whereby multiple copies of the complementary sequence of the target sequence are produced.

In another embodiment, the invention provides for a method for amplifying a target nucleic acid sequence comprising a target nucleic acid, the method comprising:

(a) obtaining a single-stranded DNA comprising a target nucleic acid sequence;

(b) obtaining a Riboprimer, the Riboprimer comprising ribonucleotides, wherein at least the 3'-end portion of the Riboprimers is complementary to the 3'-end portion of the target nucleic acid sequence;

(c) optionally, obtaining a blocking oligo and annealing the blocking oligo to a region of the single-stranded DNA, wherein the 5'-end of the blocking oligo that is annealed to the single-stranded DNA delimits the 3'-end of the target nucleic;

(d) annealing the Riboprimer and the blocking oligo, if a blocking oligo is used, to the single-stranded DNA;

(e) obtaining a strand-displacing DNA polymerase;

(f) primer extending the Riboprimer annealed to the single-stranded DNA with the strand-displacing DNA polymerase under strand-displacing polymerization conditions;

(g) obtaining a double-stranded complex comprising the single-stranded DNA and a primer extension product, wherein the primer extension product comprises the Riboprimer sequence in its 5'-end portion and the target sequence in its 3'-end portion;

(h) contacting the double-stranded complex with an RNase H enzyme under enzyme reaction conditions so as to release at least a portion of the Riboprimer sequence in the 5'-end portion of the primer extension product of the double-stranded complex;

(i) annealing a second Riboprimer, which is identical to the Riboprimer of step (b), to the single-stranded DNA of the double-stranded complex, wherein the second Riboprimer anneals to the single-stranded DNA at the position where the portion of the Riboprimer sequence of the primer extension product was released;

(j) primer extending the second Riboprimer annealed to the single-stranded DNA of the double-stranded complex with the strand-displacing DNA polymerase under strand-displacing polymerization conditions, so as to displace the first primer extension product from the double-stranded complex and obtain a second double-stranded complex comprising the single-stranded DNA and a second primer extension product;

(k) obtaining the primer extension product that was displaced from the double-stranded complex as a result of extending the second Riboprimer annealed to the single-stranded DNA;

(l) repeating steps b through l whereby multiple copies of the primer extension products corresponding to the target sequence are produced; and (m) optionally, detecting or quantifying the primer extension products produced and released from the double-stranded complex.

In yet another embodiment, the invention provides for a method of amplifying a target nucleic acid sequence complementary to a target nucleic acid, the method comprising:

(a) hybridizing a primer, the primer comprising a polynucleotide comprising canonical purine ribonucleotides and non-canonical 2'-fluoro-pyrimidine nucleotides, to a target nucleic acid, the target nucleic acid comprising single-stranded DNA comprising the target nucleic acid sequence;

(b) optionally, hybridizing a blocking oligo to a region of the target nucleic acid, wherein the 5'-end of the blocking oligo that is annealed to the target nucleic acid delimits the 3'-end of the extension product that is to be synthesized using the primer;

(c) extending the primer with DNA polymerase; and (d) cleaving the primer with an RNase H enzyme so as to liberate at least a portion of the primer-binding site on the target nucleic acid to which the primer is complementary, such that another primer hybridizes to the primer binding site on the target nucleic acid and repeats primer extension by strand displacement, whereby multiple copies of the complementary sequence to the target sequence are produced.

Strand-displacement methods of the present invention can be combined with use of other methods in the art, such as, but not limited to methods that add a promoter or protopromoter sequence for an RNA polymerase, such as an N4 mini-vRNAP or T7 RNAP or another T7-type RNAP, in order to obtain additional transcription-based amplification of a target sequence. These methods are further characterized and supported by the detailed descriptions hereinbelow.

Riboprimers of the Invention

A Riboprimer (or Riboprimer oligo) of the invention is defined herein as an oligonucleotide comprised of four or more ribonucleotides, preferably about 10 to 200 ribonucleotides, and most preferably about 20 to 50 ribonucleotides, but there is no defined limit to the length of a Riboprimer. The exact size will depend on many factors, including the type and length of the target nucleic acid and the type and length of the target sequence that is replicated using the method. The exact size of the Riboprimer will also depend on the mode of performance of the method, including whether it is performed in a stepwise fashion or in a continuous fashion, with all steps occurring in the same reaction mixture without further addition of reagents or reaction substrates or components. If a target sequence is long and the purpose for which the method is used does not require a multiplicity of products of similar size which span approximately the entire length of the target sequence, a method of the invention can also use multiple Riboprimers to amplify a single target sequence in various portions, which could be used, for example, as a multiplicity of probes for a particular target sequence. Multiple Riboprimers can also be used in a single reaction mixture to amplify multiple different non-contiguous target sequences in a sample, which can be for the same or different target nucleic acids.

At least a portion of a Riboprimer of the invention comprises a sequence that is complementary to the 3'-end portion of a target sequence that is desired to be amplified, which target-complementary sequence comprises at least the 3'-end portion of the Riboprimer. The target-complementary sequence at the 3'-end portion of a Riboprimer can be a sequence that is complementary to one specific target sequence or the target-complementary portion of a Riboprimer can comprise an oligo(dU)$_n$ sequence, or an anchored oligo(dU)$_n$X sequence or a randomized sequence in order to amplify a multiplicity of target sequences, such as, but not limited to target sequences comprising all mRNA targets in a sample. The 3'-end portion that is complementary to the target sequence must be of sufficient length and have a composition (i.e., $T_m$) so that the 3'-end portion of the Riboprimer anneals to the target sequence under the annealing conditions of the reaction so as to permit primer extension by the strand-displacing DNA polymerase used.

The entire sequence of the Riboprimer can be complementary to the 3'-end portion of the target sequence, or only a portion of the Riboprimer, i.e., the 3'-end portion, can be complementary to the target sequence, in which case, the 5'-end portion of the Riboprimer need not be complementary to the target sequence. The target sequence that is amplified using a method of the invention can be identical to a target sequence in the target nucleic acid in a sample or it can be a sequence that is complementary to that of the target nucleic acid in the sample. In other words, the template strand for a strand-displacement replication reaction of the invention can be first-strand cDNA or second-strand cDNA.

One reason to use a Riboprimer with a 5'-portion that is not complementary to the target sequence is to provide a sequence that can be copied by second-strand primer extension using as a template a first-strand cDNA primer extension product made using the Riboprimer. Thus, the resulting second-strand cDNA will have a 3'-end portion comprising a sequence that is complementary to the 5'-portion of the Riboprimer which is not complementary to the target sequence. The additional sequences that are complementary to the 5'-portion of the Riboprimer provide an additional primer-binding site, which can provide improved amplification for some target sequences, especially if the target sequence comprises a multiplicity of target nucleic acid molecules, such as, for example, a mixture of all polyadenylated mRNA targets in a sample. Thus, some embodiments of the invention comprise use of a Riboprimer to obtain a second-strand cDNA template for strand-displacement replication, wherein the product of the reaction comprises anti-sense cDNA.

With respect to chemical composition, a Riboprimer of the present invention comprises only purine ribonucleotides and either only pyrimidine ribonucleotides or pyrimidine nucleotides wherein at least one of the pyrimidine nucleotide comprises a pyrimidine 2'-deoxyribonucleotide having a non-canonical substituent (i.e, which is not a —H or —OH substituent) on the 2'-position of the deoxyribose sugar moiety. A preferred substituent on the 2'-position of the deoxyribose sugar moiety of a pyrimidine 2'-deoxyribonucleotide is a fluorine substituent. In some embodiments of the invention, both pyrimidine 2'-deoxyribonucleotides comprise a 2'-fluoro-2'-deoxyribonucleotide, which confers resistance to many common A-type ribonucleases (which specifically cut RNA at pyrimidine nucleotides), whereas in other embodiments, one of the pyrimidine nucleotides comprises a canonical ribonucleotide and the other pyrimidine nucleotide comprises a pyrimidine 2'-deoxyribonucleotide having a non-canonical substituent on the 2'-position of the deoxyribose sugar moiety, such as, but not limited to a 2'-fluorine substituent. A Riboprimer that has purine ribonucleotides and pyrimidine 2'-deoxyribonucleotides having a 2'-fluorine substituent can still be digested using an RNase H, such as Hybridase™ thermostable RNase, which is important to permit release of the Riboprimer portion of the primer-extended Riboprimer after DNA synthesis.

In still other embodiments, some or all of one of the pyrimidine nucleotides in a reaction comprises a 2'-deoxyribonucleotide having an amino, an azido, a methoxy, or another non-canonical substituent on the 2'-position of the deoxyribose sugar moiety. The sugar moieties having an amino or azido substituent provide a site for labeling with a fluorescent or other chemical moiety, such as, but not limited to a Cy (Cyanine) dye, that permits detection of the strand-displacement products when they are used as a probe (i.e., for gene expression screening using an array or microarray). Many chemicals and methods for labeling a probe are well known in art. The invention is not limited with respect to the method for labeling a probe. It is envisioned that any chemical or method that results in a detectable signal for an intended purpose can be used. Riboprimers can be synthesized using an oligonucleotide synthesizer using methods known in the art or they can be purchased from commercial sources such as TriLink Biotechnologies (San Diego, Calif.) or Integrated DNA Technologies (Coralville, Iowa). Alternatively, Riboprimers can be synthesized in high yields by in vitro transcription. Riboprimers comprising only ribonucleotides can be synthesized using the AmpliScribe™ T7-Flash™ Transcription Kit according to the instructions of the manufacturer (EPICENTRE Technologies, Madison, Wis.). Riboprimers comprising purine ribonucleotides and pyrimidine 2'-fluoro-2'-deoxyribonucleotides can be synthesized using a DuraScribe™ T7 Transcription Kit according to the instructions of the manufacturer (EPICENTRE Technologies, Madison, Wis.). Riboprimers comprising purine ribonucleotides and pyrimidine nucleotides having other 2'-substituents on the 2'-deoxyribose sugar moiety can be synthesized using a T7 R&DNA™ Polymerase (EPICENTRE Technologies, Madison, Wis.), or a another suitable enzyme, as disclosed in U.S. Pat. Nos. 5,849,546 and U.S. patent application No. 20010049097, both incorporated herein by reference. Riboprimers containing 2'-azido-2'-deoxyribonucleotides and some other modified nucleotides can be synthesized using the Y639F/H784A double mutant T7 RNA polymerase enzyme described by Padilla and Sousa (Nucleic Acids Res., 30: e138, 2002, incorporated herein by reference).

Strand-Displacing DNA Polymerases of the Invention

A "DNA-dependent DNA polymerase" is an enzyme that synthesizes a complementary DNA ("cDNA") copy from a DNA template. Examples are DNA polymerase I from *E. coli* and bacteriophage T7 DNA polymerase. All known DNA-dependent DNA polymerases require a complementary primer to initiate synthesis. It is known that under suitable conditions a DNA-dependent DNA polymerase may synthesize (i.e., "reverse transcribe") a complementary DNA copy from an RNA template, a process that is also referred to as "reverse transcription."

Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." The template for strand displacement DNA synthesis using a method of the invention can be a linear or circular ssDNA. If the DNA template is a single-stranded circle, primed DNA synthesis procedes around and around the circle, with continual displacement of the strand ahead of the replicating strand, a process called "rolling circle replication." Rolling circle replication results in synthesis of tandem copies of the circular template. The suitability of a DNA polymerase for use in an embodiment of the invention that comprises strand displacement on linear templates or rolling circle replication can be readily determined by assessing its ability to carry out rolling circle replication. By way of example, but not of limitation, the ability of a polymerase to carry out rolling circle replication can be determined by using the polymerase in a rolling circle replication assay such as those described by Fire and Xu (Proc. Natl. Acad. Sci. USA, 92: 4641-4645, 1995), incorporated herein by reference. It is preferred that a DNA polymerase be a strand displacing DNA polymerase and lack a 5'-to-3' exonuclease activity for strand displacement polymerization reactions using both linear or circular templates since a 5'-to-3' exonuclease activity, if present, might result in the destruction of the synthesized strand. It is also preferred that DNA polymerases for use in the disclosed strand displacement synthesis methods are highly processive. The ability of a DNA polymerase to strand-displace can vary with reaction conditions, in addition to the particular enzyme used. Strand displacement and DNA polymerase processivity can also be assayed using methods described in Kong et al (J. Biol. Chem., 268: 1965-1975, 1993 and references cited therein, all of which are incorporated herein by reference).

Preferred strand displacing DNA polymerases of the invention are rBst DNA polymerase large fragment (Iso-Therm™ DNA polymerase, available from EPICENTRE Technologies, Madison, Wis., USA), BcaBEST™ DNA polymerase (Takara Shuzo Co., Kyoto, Japan), RepliPHI™ phi29 DNA polymerase (U.S. Pat. Nos. 5,576,204 and 5,001,050 to Blanco et al., incorporated herein by reference; phi29 is available under the trademark name RepliPHI™ from Epicentre Technologies, Madison, Wis., USA), SequiTherm™ DNA polymerase (EPICENTRE Technologies, Madison, Wis., USA). Other strand-displacing DNA polymerases which can be used include, but are not limited to, phage M2 DNA polymerase (Matsumoto et al., Gene, 84: 247, 1989), phage ΦPRD1 DNA polymerase (Jung et al., Proc. Natl. Acad. Sci. USA, 84: 8287, 1987), VENT® DNA polymerase (Kong et al., J. Biol. Chem. 268: 1965-1975, 1993), Klenow fragment of DNA polymerase I (Jacobsen et al., Eur. J. Biochem. 45: 623-627, 1974), T5 DNA polymerase (Chatterjee et al., Gene 97:13-19, 1991), PRD1 DNA polymerase (Zhu and Ito, Biochim. Biophys. Acta, 1219: 267-276, 1994), modified T7 DNA polymerase (Tabor and Richardson, J. Biol. Chem., 262: 15,330-15,333, 1987); Tabor and Richardson, J. Biol. Chem., 264: 6447-6458, 1989); Sequenase™ (U.S. Biochemicals, Cleveland, Ohio, USA), and T4 DNA polymerase holoenzyme (Kaboord and Benkovic, Curr. Biol., 5: 149-157, 1995), all of which references are incorporated herein by reference. IsoTherm™ DNA polymerase (rBst DNA polymerase large fragment; EPICENTRE) is most preferred because, in addition to having strand-displacing DNA polymerase activity, it can also be used as a reverse transcriptase for synthesis of first-strand cDNA from RNA target nucleic acids (e.g., U.S. Pat. No. 6,030,814 of Jendrisak et al., incorporated herein by reference). BcaBEST™ DNA polymerase (Takara Shuzo Co., Kyoto, Japan) can also be used as a reverse transcriptase as well as a strand-displacing DNA polymerase.

In general, it is desirable that the amount of strand-displacing DNA polymerase in the reaction be as high as possible without inhibiting the reaction. By way of example, but without limitation, IsoTherm™ DNA Polymerase can be used at about 50 units to about 100 units in a 50-microliter reaction. Since definitions for units vary for different DNA polymerases and even for similar DNA polymerases from different vendors or sources, and also because the activity for each enzyme varies at different temperatures and under different reaction conditions, it is desirable to optimize the amount of strand-displacing DNA polymerase and reaction conditions for each target sequence and Riboprimer used.

Strand displacement can be facilitated through the use of a strand displacement factor, such as helicase. It is considered that any DNA polymerase that can perform rolling circle replication in the presence of a strand displacement factor is suitable for use in embodiments of the invention that comprise strand displacement, even if the DNA polymerase does not perform rolling circle replication in the absence of such a factor. Strand displacement factors that permit rolling circle replication include, but are not limited to, BMRF1 polymerase accessory subunit (Tsurumi et al., J. Virology, 67: 7648-7653, 1993), adenovirus DNA-binding protein (Zijderveld and van der Vliet, J. Virology, 68: 1158-1164, 1994), herpes simplex viral protein ICP8 (Boehmer and Lehman, J. Virology, 67: 711-715, 1993); Skaliter and Lehman, Proc. Natl. Acad. Sci. USA, 91: 10,665-10,669, 1994), single-stranded DNA binding proteins (SSB; Rigler and Romano, J. Biol. Chem., 270: 8910-8919, 1995), and calf thymus helicase (Siegel et al., J. Biol Chem., 267: 13,629-13,635, 1992), all of which are incorporated herein by reference.

RNase H Enzymes of the Invention

"Ribonuclease H" or "RNase H" is an enzyme that degrades the RNA portion of an RNA:DNA duplex (or complex). An RNase H can be an endonuclease or an exonuclease. An RNase H enzyme that has endonuclease activity is preferred for the present invention. The degradation may result in separation of RNA from an RNA:DNA complex. Alternatively, the RNase H may simply cut the RNA at various locations such that portions of the RNA melt off or permit enzymes to unwind portions of the RNA. When used in an embodiment of the invention, RNaseH enzymes that can be used include, but are not limited to, E. coli RNase H, or Hybridase™ Thermostable RNase H (EPICENTRE Technologies, Madison, Wis.), Thermus thermophilus RNase H or Thermus flavus RNase H (U.S. Pat. Nos. 5,268,289; 5,459, 055; and 5,500,370, incorporated herein by reference). The latter enzymes that are thermostable, and therefore, maintain more consistent activity in reactions and are more easily stored and shipped, are preferred in most embodiments of the invention. Other RNase H enzymes that can be used are those that are described by Sagawa et al., in PCT Patent Publication No. WO 02/16639; and in PCT Patent Publications Nos. WO 00/56877 and AU 00/29742, all of which are incorporated herein by reference. However, in other embodiments it is desired to use a less thermally stable enzyme, such as E. coli RNase H, because it is easier to inactivate the enzyme in a reaction mixture. In general, it is preferred that the RNase H enzyme used does not also have DNA polymerase activity and that the strand-displacing DNA polymerase used for a strand displacement replication reaction of the present invention does not have RNase H activity.

In general, it is desirable that the amount of RNase H in a Riboprimer strand-displacement replication reaction be as low as possible, so long as the amount of RNase H used liberates the Riboprimer-binding site on the target sequence so that another Riboprimer can anneal thereto with sufficient efficiency that strand-displacement replication occurs. The amount of RNAse H that should be used also depends on the length and composition of the target-complementary 3'-end portion of the Riboprimer used. As discussed elsewhere herein, sites of cleavage by RNase H vary according to the particular sequence. Also, the presence of 2'-substituents (such as a 2'-flourine substituent) on sugar moieties of the target-complementary portion of the Riboprimer can decrease the rate cleavage by a particular RNase H enzyme. The ratio of strand-displacing DNA polymerase to RNase H enzyme in a strand displacement replication reaction of the invention also must be optimized. Thus, it is important that the reaction comprises sufficient DNA polymerase so that primer extension of the Riboprimer occurs at a faster rate than digestion of the target-complementary portion of the Riboprimer that is annealed to the target sequence. Based on reading the present specification of the invention, a person with knowledge in the art will understand and know how to adjust for different variables in a strand displacement replication reaction.

By way of example, but without limitation, if IsoTherm™ DNA Polymerase is used at about 50 units to about 100 units in a 50-microliter strand displacement replication reaction, Hybridase™ Thermostable RNase H can be used in the reaction at about 0.001 to about 0.1 units. Since definitions for units vary for different DNA polymerase and RNase H enzymes and even for similar enzymes from different vendors or sources, and also because the activity for each enzyme varies at different temperatures and under different reaction conditions, a person with knowledge in the art will know that it is desirable to optimize the amounts and ratio of strand-displacing DNA polymerase RNase H enzyme and other reaction conditions for each target sequence and Riboprimer used.

Kacian et al., disclosed in U.S. Pat. No. 5,399,491, incorporated herein by reference, that the number, distribution, and position of putative RNase H cut sites determine, in part, the usefulness of a given primer and that amplification can be improved by inclusion of intentional mismatches or insertion of sequences between a transcription promoter and primer in order to affect the number, distribution, and position of putative RNase H cut sites. Thus, in preferred processes of the invention for removing RNA from RNA:DNA hybrids following reverse transcription to make first-strand cDNA if an RNA target is used, the RNA target sequence is determined and then analyzed to determine where RNase H degradation will cause cuts or removal of sections of RNA from the duplex upon synthesis of first-strand cDNA. The processes of the invention include conducting experiments to determine the effect on amplification of the target sequence of the degradation of the RNA target sequence by RNase H present in the reverse transcriptase used, including, but not limited to, AMV reverse transcriptase, and both RNase H-plus and RNase H-minus MMLV reverse transcriptase. The information of Kacian et al., can also be used with respect to designing the optimal target-complementary portion of Riboprimers of the invention related to the RNase H specificities of cut sites for particular enzymes, including E. coli RNase H or thermostable RNase H enzymes that are stable for more than 10 minutes at 70° C. (U.S. Pat. Nos. 5,268,289; 5,459,055; and 5,500,370, incorporated herein by reference), such as, but not limited to Hybridase™ thermostable RNase H (EPICENTRE Technologies, Madison, Wis., USA), Tth RNase H, and Tfl RNase H.

With respect to strand displacement replication methods of the invention, the processes of the invention include conducting experiments to determine the optimal amount of an RNase H enzyme to use in a strand displacement replication reaction mixture on amplification of the target sequence and degradation of strand-displacement primers comprising RNA or modified RNA (e.g., primers containing 2'-F-dCTP and 2'-F-dUTP that are made using the DuraScribe™ Transcription Kit). Preferred embodiments of strand displacement replication reactions will use the minimum concentration of an RNase H to achieve optimal strand displacement. A thermostable RNase H, such as Hybridase™ RNase H is preferred because it is stable and enzymatic activity is more constant throughout the reaction, making it easier to titrate an optimal level of the enzyme.

Reaction Conditions and Detection Methods of the Invention

Appropriate reaction media and conditions for carrying out the methods of the present invention are those that permit nucleic acid amplification according to the methods of the present invention. Such media and conditions are known to persons of skill in the art, and are described in various publications, such as U.S. Pat. No. 5,679,512 and PCT Pub. No. W099/42618, incorporated herein by reference. For example, a buffer can be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 10 mM, and most preferably from about 1 to 6 mM. The reaction medium can also include other salts, such as KCl, that contribute to the total ionic strength of the medium. For example, the range of a salt such as KCl is preferably from about 0 to about 100 mM, more preferably from about 0 to about 75 mM, and most preferably from about 0 to about 50 mM. The reaction medium can further include additives that could affect performance of the amplification reactions, but that are not integral to the activity of the enzyme components of the methods. Such additives include proteins such as BSA, and non-ionic detergents such as NP40 or Triton. Reagents, such as DTT, that are capable of maintaining activities enzyme with sulfhydryl groups can also be included. Such reagents are known in the art. Where appropriate, an RNase inhibitor, such as, but not limited to a placental ribonuclease inhibitor (e.g., RNasin™, Promega Corporation, Madison, Wis., USA) or an antibody RNase inhibitor, that does not inhibit the activity of an RNase employed in the method can also be included. Any aspect of the methods of the present invention can occur at the same or varying temperatures. Preferably, the reactions are performed isothermally, which avoids the cumbersome thermocycling process. The amplification reaction is carried out at a temperature that permits hybridization of the oligonucleotides of the present invention to the target sequence and/or first-strand cDNA of a method of the invention and that does not substantially inhibit the activity of the enzymes employed. The temperature can be in the range of preferably about 25° C. to about 85° C., more preferably about 30° C. to about 75° C., and most preferably about 37° C. to about 70° C. In these processes, the temperature of the transcription steps can be in the range of preferably about 25° C. to about 85° C., more preferably about 30° C. to about 75° C., and most preferably about 37° C. to about 55° C.

As disclosed in U.S. Pat. Nos. 6,048,696 and 6,030,814, as well as in German Pat. No. DE4411588C1, all of which are incorporated herein by reference and made part of the present invention, it is preferred in many embodiments to use a final concentration of about 0.25 M, about 0.5 M, about 1.0 M, about 1.5 M, about 2.0 M, about 2.5 M or between about 0.25 M and 2.5 M betaine (trimethylglycine) in DNA polymerase or reverse transcriptase reactions in order to decrease DNA polymerase stops and increase the specificity of reactions which use a DNA polymerase.

Nucleotide and/or nucleotide analogs, such as deoxyribonucleoside triphosphates, that can be employed for synthesis of reverse transcription or primer extension products in the methods of the invention are provided in an amount that is determined to be optimal or useful for a particular intended use. The oligonucleotide components of amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Riboprimers and other primers used within the present invention can each be provided at about or at least about any of the following concentrations: 50 nM, 100 nM, 500 nM, 1000 nM, 2500 nM, 5000 nM, or 10,000 nM, but higher or lower concentrations can also be used. By way of example, but not of limitation, a concentration of one or more oligonucleotides may be desirable for production of one or more target nucleic acid sequences that are used in another application or process. The invention is not limited to a particular concentration of an oligonucleotide, so long as the concentration is effective in a particular method of the invention. In some embodiments, the foregoing components are added simultaneously at the initiation of the amplification process.

In other embodiments, components are added in any order prior to or after appropriate time points during the amplification process, as required and/or permitted by the amplification reaction. Such time points can readily be identified by a person of skill in the art. The enzymes used for nucleic acid amplification according to the methods of the present invention are generally added to the reaction mixture following a step for denaturation of a double-stranded target nucleic acid in or from a sample, and/or following hybridization of primers and/or oligos of a reaction to a denatured double-stranded or single-stranded target nucleic acid, as determined by their thermal stability and/or other considerations known to the person of skill in the art.

The amplification reactions can be stopped at various time points, and resumed at a later time. The time points can readily be identified by a person of skill in the art. Methods for stopping the reactions are known in the art, including, for example, cooling the reaction mixture to a temperature that inhibits enzyme activity. Methods for resuming the reactions are also known in the art, including, for example, raising the temperature of the reaction mixture to a temperature that permits enzyme activity. In some embodiments, one or more of the components of the reactions is replenished prior to, at, or following the resumption of the reactions. Alternatively, the reaction can be allowed to proceed (i.e., from start to finish) without interruption.

In some embodiments, the detection of the amplification product is indicative of the presence of the target sequence.

Quantitative analysis, including analysis in real time, can also be performed in some embodiments. Direct and indirect detection methods (including quantification) are well known in the art. For example, the amount of target sequence in a test sample can be determined by comparing the amount of product amplified from a test sample containing an unknown amount of a polynucleotide having a target sequence to the amplification product of a reference sample that has a known quantity of a polynucleotide with the target sequence. The amplification methods of the present invention can also be extended to analysis of sequence alterations and sequencing of the target nucleic acid. The amplified nucleic acid can be sequenced using any suitable procedure. Many such procedures are known. Preferred forms of sequencing for use with amplified sequences produced from some embodiments are nanosequencing methods described by Jalanko et al., Clinical Chemistry 38: 39-43 (1992); Nikiforov et al., Nucleic Acids Research, 22: 4167-4175 (1994); and Kobayashi et al., Molecular and Cellular Probes, 9: 175-182 (1995), and primer extension sequencing, as described in PCT Application WO 97/20948, all of which references are included herein by reference. Further, detection could be effected by, for example, examination of translation products from RNA amplification products.

Kits and Compositions of the Invention

Important compositions of the invention are Riboprimers. A Riboprimer can be provided for strand-displacement replication of one specific target sequence or a Riboprimer can be provided for amplifying a multiplicity of target sequences, such as, but not limited to target sequences comprising all mRNA targets in a sample. In the latter case, a Riboprimer oligo can be provided that comprises an oligo(dU)$_n$ sequence, or an anchored oligo(dU)$_n$X sequence, or a randomized sequence. Still further multiple specific Riboprimers can be provided in order to permit amplification of multiple different target sequences in the same sample.

A kit of the invention can comprise one or more Riboprimers and instructions for their use in a method of the invention.

A kit of the invention can also comprise all of the enzymes, including a strand-displacing DNA polymerase, such as, but not limited to IsoTherm™ DNA Polymerase or RepliPHI™ phi29 DNA Polymerase phi29 DNA Polymerase (U.S. Pat. Nos. 5,576,204 and 5,001,050 to Blanco et al., incorporated herein by reference; phi29 is available under the trademark name RepliPHI™ from Epicentre Technologies, Madison, Wis., USA), and a Ribonuclease H enzyme, such as but not limited to Hybridase™ Thermostable RNase H (all from EPICENTRE Technologies, Madison, Wis.), which are needed for carrying out a strand displacement replication (SDR) method of the invention. The enzymes can be provided in the kit separately or combined into a single ready-to-use solution containing the optimal ratio of each enzyme. A kit comprising enzymes for Riboprimer-SDR can also comprise a Riboprimer, or a kit comprising enzymes for Riboprimer-SDR can be provided without a Riboprimer for customers who wish to prepare their own Riboprimers for a specific target sequence. Another embodiment of a kit of the invention comprises a DNA polymerase and a RNase H enzyme for performing Riboprimer SDR, at least one Riboprimer, and a reaction solution that contains an optimal level of betaine for performing Riboprimer SDR with the specific Riboprimers in the kit.

A kit of the invention may also optionally comprise additional components, such as reaction buffers, control substrates, size markers, reagents and instructions to detect the products of a reaction, and the like, all of which are provided in quantites to match the need for each component for the number of intended reactions. Still further, a kit may optionally contain detailed instructions/protocols and troubleshooting guides.

EXAMPLE 1

Strand Displacement Replication of ssDNA Template

The template used was a 2 kb concatemeric ssDNA comprising poly-U binding sites. 100 picomoles of a mixture of 16 different Riboprimers comprising 18 ribonucleotides each were obtained. The Riboprimers comprised $U_{16}NN$, wherein "N" means A, C, G, or U. In addition, a control primer comprising DNA was obtained. Within separate reactions, the Riboprimers and the control primer were annealed to 20 ng of the template DNA by incubating the primers with the template DNA for 30 seconds at 95° C. followed by cooling on ice.

A reaction mixture comprising dATP, dCTP, dGTP, and dTTP (each at 0.25 mM final concentration), DTT (dithiothreitol, 4 mM final concentration), 4 units of RNasin™ Plus (Promega Corporation, Madison, Wis., USA), bovine serum albumin (0.2 mg/ml final concentration), 0.02 units of RNase H (Hybridase™, Epicentre Technologies, Madison, Wis., USA), 0.2 µg of Single-Stranded DNA Binding Protein (SSB, Epicentre Technologies, Madison, Wis., USA), and 1 µg of phi29 DNA polymerase was added to the primer-template complexes such that the final volumes were 20 microliter. The reactions were incubated at 30° C. for 16 hours, followed by heating at 95° C. for 5 minutes. Aliquots of 4 mircoliter each were analyzed on an ethidium bromide stained 2% TAE agarose gel.

Figure 3:
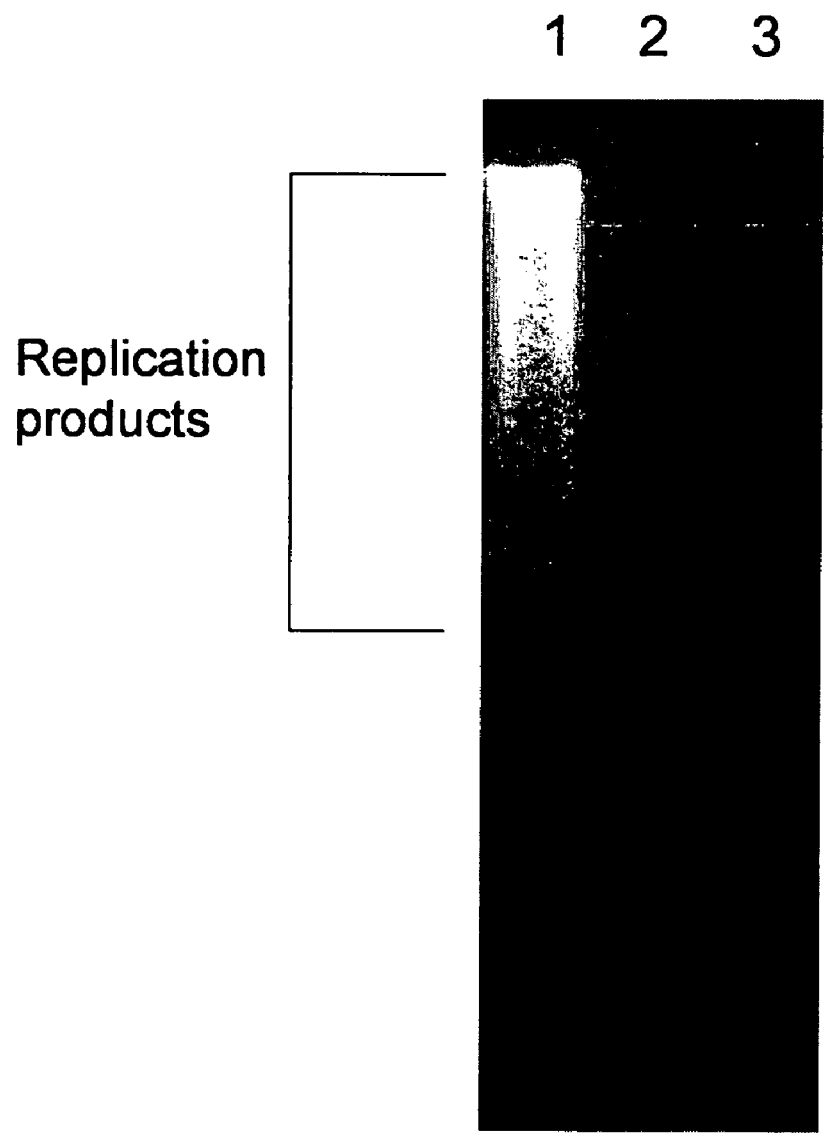
FIG. 3. Ethidium bromide stained agarose gel of strand displacement replication products of a ssDNA template. The strand-displacement replication reaction comprised obtaining Riboprimers.

Replication products were observed on the gel (FIG. 3, lane 1), indicating efficient replication. No replication products were observed when no template DNA molecule was added (FIG. 3, lane 2) or when the control primer comprising DNA added instead of the Riboprimers (FIG. 3, lane 3).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for amplifying a target nucleic acid sequence comprising a target nucleic acid, the method comprising the steps of:
   a) hybridizing a riboprimer to a DNA template comprising the target nucleic acid sequence, wherein said riboprimer comprises: i) only ribonucleotides, or ii) only purine ribonucleotides and only pyrimidine nucleotides, wherein at least one of the pyrimidine nucleotides is a pyrimidine 2'-deoxyribonucleotide having a non-canonical substituent, which substituent is neither an H nor an OH, on the 2'-position of the deoxyribose sugar moiety;
   b) extending the riboprimer with a DNA polymerase that lacks 5'-to-3' exonuclease activity; and
   c) cleaving the annealed riboprimer with an RNAse H enzyme such that another riboprimer hybridizes to the template and repeats primer extension, whereby multiple copies of the complementary sequence of the target nucleic acid sequence are produced.

2. The method of claim 1, further comprising, prior to step (b), the step of hybridizing a blocking oligonucleotide to a region of the template that is 5' with respect to hybridization of the riboprimer to the template.

3. The method of claim 1, wherein the method is conducted under isothermal conditions.

4. The method of claim 1, further comprising the step of:
c) attaching the multiple copies produced in step c) onto a solid substrate to make a microarray of the multiple copies.

5. The method of claim 1, further comprising the step of hybridizing the multiple copies produced in step c) to a microarray of nucleic acid molecules immobilized on a surface of a solid phase.

6. The method of claim 1, wherein step (b) comprises utilization of at least one type of labeled dNTP such that labeled extension products are generated.

7. The method of claim 1, wherein the riboprimer comprises AMP, GMP, 2'-F-dUMP, and 2'-F-dCMP.

8. The method of claim 1, wherein a plurality of riboprimers is used.

9. The method of claim 1, wherein the riboprimer comprises only ribonucleotides.

10. The method of claim 1, wherein the 2'-substituent is selected from the group consisting of a fluorine substituent, an amino substituent, a methoxy substituent, and an azido substituent.

11. The method of claim 1, wherein the riboprimer comprises purine ribonucleotides and pyrimidine 2'-fluoro-2'-deoxyribonucleotides.

12. The method of claim 1, wherein the entire sequence of the riboprimer is complementary to the 3'-end portion of the target sequence.

13. The method of claim 1, wherein the 5'-end portion of the riboprimer is not complementary to the target nucleic acid sequence.

14. The method of claim 13, wherein the non-complementary 5' end portion provides a sequence that can be copied by second-strand primer extension using as a template a first-strand cDNA primer extension product made using the riboprimer.

15. The method of claim 13 wherein the target-complementary sequence at the 3'-end portion of the riboprimer comprises a randomized sequence.

16. The method of claim 2, wherein the blocking oligo comprises a peptide nucleic acid (PNA).

17. The method of claim 1, wherein the DNA polymerase is selected from the group consisting of BST DNA polymerase large fragment (ISOTHERM), SEQUITHERM DNA polymerase (EPICENTRE Technologies), BCABEST DNA polymerase (Takara Shuzo Co.), phi29 DNA polymerase, and Exo-minus Klenow DNA polymerase.

18. The method of claim 1, wherein the RNase H enzyme is a thermostable RNase H.

19. The method of claim 18, wherein said thermostable RNase H is selected from the group consisting of HYBRIDASE thermostable RNase H (EPICENTRE Technologies), Tth RNase H, and Tfl RNase H.

20. The method of claim 1, wherein said RNase H is E. coli RNase H.

21. A method for amplifying a target nucleic acid sequence comprising a target nucleic acid, the method comprising:
a) obtaining a DNA comprising a target nucleic acid sequence;
b) obtaining a riboprimer, the riboprimer comprising: i) only ribonucleotides, or ii) only purine ribonucleotides and only pyrimidine nucleotides, wherein at least one of the pyrimidine nucleotides is a pyrimidine 2'-deoxyribonucleotide having a non-canonical substituent, which substituent is neither an H nor an OH, on the 2'-position of the deoxyribose sugar moiety, and wherein at least the 3'-end portion of the riboprimer is complementary to a portion of the target nucleic acid sequence;
c) annealing the riboprimer to the DNA;
d) obtaining a strand-displacing DNA polymerase that lacks 5'-to-3' exonuclease activity;
e) primer extending the riboprimer annealed to the DNA with the strand-displacing DNA polymerase under strand-displacing polymerization conditions;
f) obtaining a double-stranded complex comprising the DNA and a primer extension product, wherein the primer extension product comprises the riboprimer sequence in its 5'-end portion and the target sequence in its 3'-end portion;
g) contacting the double-stranded complex with an RNase H enzyme under enzyme reaction conditions so as to release at least a portion of the riboprimer sequence in the 5'-end portion of the primer extension product of the double-stranded complex;
h) annealing a second riboprimer to the single-stranded DNA of the double-stranded complex, wherein the second riboprimer anneals to the single-stranded DNA at the position where the portion of the riboprimer sequence of the primer extension product was released;
i) primer extending the second riboprimer annealed to the single-stranded DNA of the double-stranded complex with the strand-displacing DNA polymerase under strand-displacing polymerization conditions, so as to displace the first primer extension product from the double-stranded complex and obtain a second double-stranded complex comprising the single-stranded DNA and a second primer extension product; and
j) obtaining the primer extension product that was displaced from the double-stranded complex as a result of extending the second riboprimer annealed to the single-stranded DNA.

22. The method of claim 21, further comprising the step of annealing a blocking oligo to a region of the DNA, wherein the 5'-end of the blocking oligo that is annealed to the single-stranded DNA delimits the 3'-end of the target nucleic acid sequence.

23. The method of claim 21, further comprising step k) repeating steps b through j whereby multiple copies of the primer extension products corresponding to the target sequence are produced.

24. The method of claim 21 further comprising step l) detecting the primer extension products produced.

25. The method of claim 21, further comprising step l) quantifying the primer extension products.

26. The method of claim 21, wherein a plurality of riboprimers is used.

27. The method of claim 21, wherein the riboprimer comprises only ribonucleotides.

28. The method of claim 21, wherein the 2'-substituent is selected from the group consisting of a fluorine substituent, an amino substituent, a methoxy substituent, and an azido substituent.

29. The method of claim 21, wherein the riboprimer comprises purine ribonucleotides and pyrimidine 2'-fluoro-2'-deoxyribonucleotides.

30. The method of claim 21, wherein the entire sequence of the riboprimer is complementary to the 3'-end portion of the target sequence.

31. The method of claim 21, wherein the 5'-end portion of the riboprimer is not complementary to the target nucleic acid sequence.

32. The method of claim 31, wherein the non-complementary 5' end portion provides a sequence that can be copied by second-strand primer extension using as a template a first-strand cDNA primer extension product made using the riboprimer.

33. The method of claim 31, wherein the target-complementary sequence at the 3'-end portion of the riboprimer comprises a randomized sequence.

34. The method of claim 22, wherein the blocking oligo comprises a peptide nucleic acid (PNA).

35. The method of claim 21, wherein the DNA polymerase is selected from the group consisting of BST DNA polymerase large fragment (ISOTHERM), SEQUITHERM DNA polymerase (EPICENTRE Technologies), BCABEST DNA polymerase (Takara Shuzo Co.), phi29 DNA polymerase, and Exo-minus Klenow DNA polymerase.

36. The method of claim 21, wherein the RNase H enzyme is a thermostable RNase H.

37. The method of claim 36, wherein said thermostable RNase H is selected from the group consisting of HYBRIDASE thermostable RNase H (EPICENTRE Technologies), Tth RNase H, and Tfl RNase H.

38. The method of claim 21, wherein said RNase H is *E. coli* RNase H.

39. A method of generating multiple copies of a polynucleotide sequence complementary to an RNA sequence of interest, the method comprising the steps of:
   a) extending a first primer hybridized to a target RNA with an RNA-dependent DNA polymerase, wherein the first primer is a riboprimer, wherein said riboprimer comprises: i) only ribonucleotides, or ii) only purine ribonucleotides and only pyrimidine nucleotides, wherein at least one of the pyrimidine nucleotides is a pyrimidine 2'-deoxyribonucleotide having a non-canonical substituent, which substituent is neither an H nor an OH, on the 2'-position of the deoxyribose sugar moiety, and whereby a complex comprising a first primer extension product and the target RNA is produced;
   b) cleaving RNA in the complex of step (a) with an RNase H enzyme;
   c) extending a second primer hybridized to the first primer extension product with a DNA-dependent DNA polymerase that lacks 5'-to-3' exonuclease activity, wherein said second primer is a riboprimer comprising: i) only ribonucleotides, or ii) only purine ribonucleotides and only pyrimidine nucleotides, wherein at least one of the pyrimidine nucleotides is a pyrimidine 2'-deoxyribonucleotide having a non-canonical substituent, which substituent is neither an H nor an OH, on the 2'-position of the deoxyribose sugar moiety, and whereby a second primer extension product is produced to form a complex of first and second primer extension products;
   d) cleaving the riboprimer in the complex of first and second primer extension products with an RNase H enzyme such that a riboprimer hybridizes to the second primer extension product; and
   e) extending the riboprimer hybridized to the second primer extension product with a DNA-dependent DNA polymerase, whereby the first primer extension product is displaced and multiple copies of a polynucleotide sequence complementary to the RNA sequence of interest are generated.

40. The method of claim 39, wherein the RNA-dependent DNA polymerase is selected from the group consisting of Bst DNA polymerase, BST DNA polymerase large fragment (ISOTHERM), Moloney murine leukemia virus (MMLV) reverse transcriptase, and avian myeloblastosis virus (AMV) reverse transcriptase.

41. The method of claim 40, wherein said MMLV reverse transciptase comprises RNase H minus MMLV reverse transcriptase.

42. The method of claim 39, wherein a plurality of riboprimers is used to generate multiple copies of a polynucleotide sequence complementary to the RNA sequence of interest.

43. The method of claim 39, wherein a plurality of different riboprimers is used for hybridizing to the target RNA.

44. The method of claim 39, wherein the riboprimer comprises only ribonucleotides.

45. The method of claim 39, wherein the 2'-substituent is selected from the group consisting of a fluorine substituent, an amino substituent, a methoxy substituent, and an azido substituent.

46. The method of claim 39, wherein the riboprimer comprises purine ribonucleotides and pyrimidine 2'-fluoro-2'-deoxyribonucleotides.

47. The method of claim 39, wherein the riboprimer comprises AMP, GMP, 2'-F-dUMP, and 2'-F-dCMP.

48. The method of claim 39, wherein the riboprimer that hybridizes to the target RNA comprises a poly-U sequence.

49. The method of claim 39, wherein the riboprimer that hybridizes to the target RNA is a random primer.

50. The method of claim 39, wherein the riboprimer that hybridizes to the target RNA comprises a 5'-portion that is not hybridizable to the target RNA under conditions under which the riboprimer hybridizes to the target RNA.

51. The method of claim 39, wherein the target RNA is mRNA.

52. The method of claim 39, wherein the RNase H enzyme is a thermostable RNase H.

53. The method of claim 52, wherein said thermostable RNase H is selected from the group consisting of HYBRIDASE thermostable RNase H (EPICENTRE Technologies), Tth RNase H, and Tfl RNase H.

54. The method of claim 39, wherein said RNase H is *E. coli* RNase H.

55. The method of claim 39, wherein the DNA polymerase is selected from the group consisting of BST DNA polymerase large fragment (ISOTHERM), SEQUITHERM DNA polymerase (EPICENTRE Technologies), BCABEST DNA polymerase (Takara Shuzo Co.), phi29 DNA polymerase, and Exo-minus Klenow DNA polymerase.

56. The method of claim 39, wherein the second primer is a random primer.

57. The method of claim 39, wherein the second primer comprises a fragment of the target RNA hybridized to the primer extension product, which fragment is generated by cleaving RNA in the complex in step (b) with an enzyme that cleaves RNA from an RNA/DNA hybrid.

58. The method of claim 39, wherein the second primer comprises DNA.

59. The method of claim 39, wherein the RNA-dependent DNA polymerase and DNA-dependent polymerase are the same enzyme.

60. The method of claim 57 wherein the RNA-dependent DNA polymerase and the enzyme that cleaves RNA from an RNA/DNA hybrid are the same enzyme.

61. The method of claim 39, further comprising the step of:
f) generating multiple copies of a polynucleotide sequence complementary to two or more different sequences of interest.

62. The method of claim 61, wherein at least two different riboprimers that hybridize to the target RNA are used.

63. The method of claim 39, further comprising the step of:
f) attaching the multiple copies onto a solid substrate to make a microarray of the multiple copies.

64. The method of claim 39, further comprising the step of:
f) hybridizing the multiple copies to a microarray of nucleic acid molecules immobilized on a surface of a solid phase.

* * * * *